US00PP10844P

United States Patent [19]

Olij

[11] Patent Number: Plant 10,844

[45] Date of Patent: Mar. 30, 1999

[54] HYBRID TEA ROSE PLANT NAMED 'OLIJBRAU'

[75] Inventor: Huibert W. Olij, Holland, Netherlands

[73] Assignee: Olij Rozen B.V., Holland, Netherlands

[21] Appl. No.: 917,173

[22] Filed: Aug. 25, 1997

[51] Int. Cl.[6] ..... A01H 5/00

[52] U.S. Cl. ..... Plt./131

[58] Field of Search ..... Plt./12, 11, 130, Plt./131

*Primary Examiner*—Howard J. Locker

*Attorney, Agent, or Firm*—Burns, Doane, Swecker & Mathis, L.L.P.

[57] ABSTRACT

A new and distinct variety of Hybrid Tea rose plant is provided which forms in abundance attractive bicolored blossoms having an unusual smoky aspect. The upper blossom surface is near dark brick red and the under surface is yellow-orange edged with red. Such blossoms are long-lasting on the plant or when cut and placed in a vase and exhibit good petal-drop characteristics. The plant exhibits an erect growth habit and forms attractive glossy dark green foliage. Good disease resistance is provided. The new variety is particularly well suited for cut flower production under greenhouse growing conditions. The blossom productivity under such growing conditions is high.

1 Drawing Sheet

SUMMARY OF THE INVENTION

The new variety of Hybrid Tea rose plant was created by artificial pollination wherein two parents were crossed which previously had been studied in the hope that they would contribute the desired characteristics. The female parent (i.e., the seed parent) of the new variety is the 'Korfan' variety (non-patented in the United States). The male parent (i.e, the pollen parent) is the 'Ruimeva' variety (U.S. Plant Pat. No. 5,820). The parentage of the new variety can be summarized as follows:

'Korfan'×'Ruimeva'.

The seeds resulting from the above pollination were sown and small plants were obtained which were physically and biologically different from each other. Selective study resulted in the identification of a single plant of the new variety.

It was found that the new variety of Hybrid Tea rose plant of the present invention possesses the following combination of characteristics:

(a) forms attractive long-lasting bicolored blossoms having a smoky aspect wherein the upper surface is near dark brick red and the under surface is yellow-orange edged with red in coloration,
(b) exhibits an erect growth habit,
(c) forms attractive dark green and glossy foliage,
(d) exhibits high blossom productivity, and
(e) is particularly well suited for cut flower production.

The new variety well meets the needs of the horticultural industry and is well adapted for cut flower production under greenhouse growing conditions.

The new variety can be readily distinguished from each of its parent varieties. Parent 'Korfan' has young blossoms that are more orange and of smaller size that are borne on shorter stems. Also, parent 'Ruimeva' forms blossoms that are more red-orange in coloration.

The new variety has been found to undergo asexual propagation in France by a number of routes, including budding, grafting, and cuttage. Asexual propagation by the above-mentioned techniques in France has shown that the characteristics of the new variety are stable and are strictly transmissible by such asexual propagation from one generation to another.

The new variety has been named the 'Olijbrau' variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were two years of age and were observed during November while budded on *Rosa indica* understock and growing in greenhouses at Le Cannet des Maures, Var, France. Dimensions in centimeters are indicated at the bottom of the photograph.

DETAILED DESCRIPTION

Figures 1, 2, 3, 4, 5, 6, 7, 8, 9, 10, 11, 12, 13, 14, 15, 16:
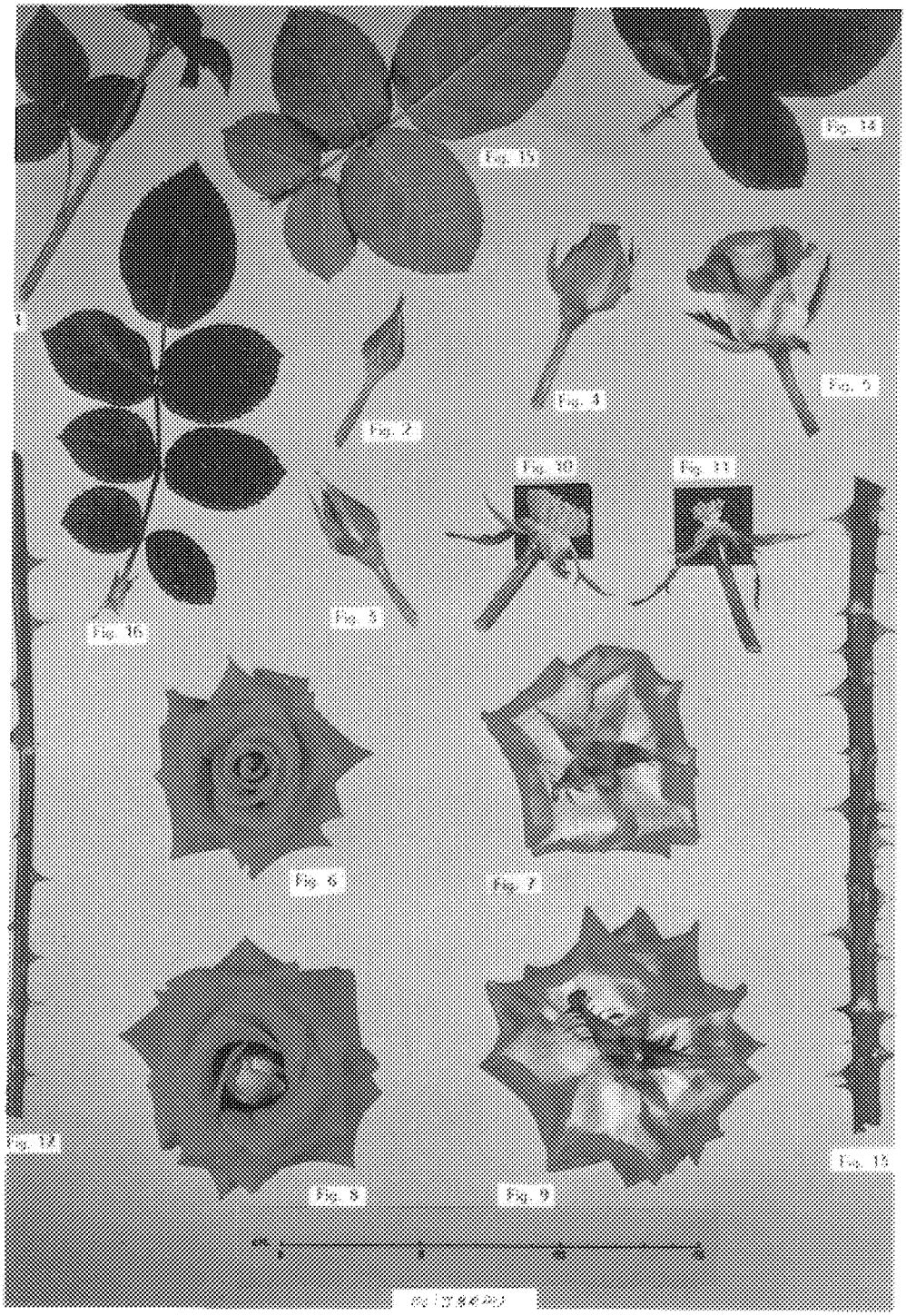
FIG. 1 illustrates a specimen of a young shoot.
FIG. 2 illustrates a specimen of a floral bud before the opening of the sepals.
FIG. 3 illustrates a specimen of a floral bud at the opening of the sepals.
FIG. 4 illustrates a specimen of a floral bud at the opening of the petals.
FIG. 5 illustrates a specimen of a flower in the course of opening.
FIG. 6 illustrates a specimen of an open flower—plan view—obverse.
FIG. 7 illustrates a specimen of an open flower—plan view—reverse.
FIG. 8 illustrates a specimen of a fully open flower—plan view—obverse.
FIG. 9 illustrates a specimen of a fully open flower—plan view—reverse.
FIG. 10 illustrates a specimen of a floral receptacle showing the arrangement of the stamens and pistils.
FIG. 11 illustrates a specimen of a floral receptacle showing the arrangement of the pistils (stamens removed)
FIG. 12 illustrates a specimen of a flowering stem.
FIG. 13 illustrates a specimen of a main branch.
FIG. 14 illustrates a specimen of a leaf with three leaflets—plan view—upper surface.
FIG. 15 illustrates a specimen of a leaf with five leaflets—plan view—under surface.
FIG. 16 illustrates a specimen of a leaf with seven leaflets—plan view—upper surface.

The chart used in the identification of the colors is that of The Royal Horticultural Society (R.H.S. Colour Chart). The description is based on the observation of two year-old plants during December while budded on *Rosa indica* understock and growing in greenhouses at Le Cannet des Maures, Var, France.

Class: Hybrid Tea.

Plant:

*Height.*—When pruned to a height of 85 cm., floral stems of approximately 50 to 70 cm. in length commonly are formed.

*Habit.*—Erect.

Branches:

*Color.*—Young stems: Yellow-Green Group 146B. Adult wood: Yellow-Green Group 147A.

*Thorns.*—Size: small. Quantity: numerous. Color: near Purple-Violet Group 80C on young stems and near Greyed-Orange Group 165D on adult wood.

*Stipules.*—Adnate, pectinate, narrow and linear.

*Petioles.*—Upper surface: striped reddish brown on young foliage, and medium green on adult foliage with glandular sides. Under surface: light green, with numerous small thorns.

*Leaflets.*—number: 3, 5 (most often), and 7. Shape: elliptic. Serration: single and regular (as illustrated). Texture: somewhat consistent. General appearance: dense, dark green, and with a glossy aspect. Color (young foliage): Upper surface: near Green Group 139A. Under surface: near Green Group 139A, and suffused with reddish brown coloration. Color (adult foliage): Upper surface: near Green Group 131A. Under surface: near Greyed-Green Group 189A.

Inflorescence:

*Number of flowers.*—usually one per stem.

*Peduncle.*—Upright, glandular, and the length is approximately 10 to 11 cm. on average.

*Sepals.*—Upper surface: tomentose, and greenish in coloration. Under surface: medium green in coloration and commonly possess extensions.

*Buds.*—Shape: conical. Length: approximately 4 cm. on average. Size: medium. Color upon opening: Upper surface: Greyed-Purple Group 185A. Under surface: Yellow-Orange Group 21D and widely suffused with Orange-Red Group 34A and 34B.

*Flower.*—Shape: substantially parallel sides with a high center. Diameter: approximately 13 cm. on average. Color (when opening begins): Upper surface: near Greyed-Purple Group 185A. Under surface: Yellow-Orange Group 21D suffused with Orange-Red Group 34B on the upper part of the petal. Color (when blooming): Upper surface: near Greyed-Red Group 178B. Under surface: near Yellow-Orange Group 17D suffused with Orange-Red Group 34B at the extremity. Color (at end of opening): Upper surface: near Greyed-Red Group 178C. Under surface: near Yellow-Orange Group 18B suffused with Orange-Red Group 34B. Fragrance: none. Lasting quality: long on the plant and when cut and placed in a vase. The blossoms commonly last approximately 7 to 8 days on the plant and approximately 8 to 10 days when cut and placed in a vase. Petal number: approximately 25 on average. Petal shape: rounded with reflexed edges. Petal drop: good with the petals commonly detaching cleanly. Stamen number: approximately 165 on average. Anthers: normal, ochre in coloration. Filaments: yellowish in coloration. Pistils: approximately 100 on average. Stigmas: strawlike in coloration. Styles: strawlike in coloration and very short. Receptacle: light green, smooth, and in longitudinal section in the shape of a pitcher.

Development:

*Vegetation.*—Strong.

*Blooming.*—Abundant. Commonly approximately 140 to 180 blossoms/square meter/year are formed under conventional greenhouse growing conditions.

*Resistance to diseases.*—Good with respect to powdery mildew and downy mildew. There is slight sensitivity to botrytis.

I claim:

1. A new and distinct variety of Hybrid Tea rose plant characterized by the following combination of characteristics:

(a) forms attractive long-lasting bicolored blossoms having a smoky aspect wherein the upper surface is near dark brick red and the under surface is yellow-orange edged with red in coloration,
(b) exhibits an erect growth habit,
(c) forms attractive dark green and glossy foliage,
(d) exhibits high blossom productivity, and
(e) is particularly well suited for cut flower production;

substantially as herein shown and described.

* * * * *